United States Patent
Bender et al.

(10) Patent No.: US 7,267,682 B1
(45) Date of Patent: Sep. 11, 2007

(54) ANASTOMOSIS STAPLE

(75) Inventors: Theodore M. Bender, San Francisco, CA (US); David L. Bombard, San Francisco, CA (US); Philipe R. Manoux, San Francisco, CA (US); Tenny Chang, Mountain View, CA (US); Jaime S. Vargas, Redwood City, CA (US); Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 646 days.

(21) Appl. No.: 10/309,519

(22) Filed: Dec. 4, 2002

(51) Int. Cl.
*A61B 17/08* (2006.01)
(52) U.S. Cl. .................. 606/219; 606/151; 606/220
(58) Field of Classification Search .............. 606/8, 606/151, 153, 213, 219, 220, 221; 411/458, 411/459, 470
See application file for complete search history.

(56) References Cited

U.S. PATENT DOCUMENTS

| | | | | |
|---|---|---|---|---|
| 431,175 A | * | 7/1890 | Southwick | 24/36 |
| 718,649 A | * | 1/1903 | Morehouse | 411/461 |
| 1,755,538 A | * | 4/1930 | Draughon | 52/551 |
| 2,111,404 A | * | 3/1938 | Pankonin | 411/444 |
| 2,174,708 A | * | 10/1939 | Sears et al. | 227/86 |
| 2,323,362 A | | 7/1943 | Weiss | |
| 2,343,525 A | * | 3/1944 | Blodgett | 24/1 |
| 2,345,053 A | | 3/1944 | Judd et al. | |
| 3,049,042 A | | 8/1962 | De Lynn | |
| 4,229,888 A | | 10/1980 | Rawson | |
| 4,340,331 A | * | 7/1982 | Savino | 411/457 |
| 4,485,816 A | * | 12/1984 | Krumme | 606/219 |
| 4,592,346 A | | 6/1986 | Jurgutis | |
| 4,610,251 A | | 9/1986 | Kumar | |
| 4,913,144 A | | 4/1990 | Del Medico | |
| 4,960,420 A | | 10/1990 | Goble et al. | |
| 5,062,753 A | | 11/1991 | Begue | |
| 5,297,714 A | * | 3/1994 | Kramer | 227/175.1 |
| 5,314,427 A | | 5/1994 | Goble et al. | |
| 5,324,307 A | * | 6/1994 | Jarrett et al. | 606/219 |
| 5,465,895 A | | 11/1995 | Knodel et al. | |
| 5,489,058 A | | 2/1996 | Plyley et al. | |
| 5,507,776 A | | 4/1996 | Hempel | |
| 5,535,935 A | | 7/1996 | Vidal et al. | |
| 5,562,241 A | | 10/1996 | Knodel et al. | |
| 5,586,711 A | | 12/1996 | Plyley et al. | |
| 5,662,258 A | | 9/1997 | Knodel | |
| 5,667,527 A | * | 9/1997 | Cook | 606/219 |

(Continued)

FOREIGN PATENT DOCUMENTS

EP        1354559 A2     5/1995

OTHER PUBLICATIONS

Atlas of Surgical Stapling, 1999, Ethicon Endo-Surgery.

(Continued)

*Primary Examiner*—Anhtuan T. Nguyen
*Assistant Examiner*—Darwin P Erezo
(74) *Attorney, Agent, or Firm*—Brian A. Schar

(57) ABSTRACT

An anastomosis staple has a base from which multiple deformable tines extend. At least one tine may be offset from at least one other tine. The tines are moveable from a first configuration to a second configuration. The staple optionally includes at least one alignment guide.

6 Claims, 6 Drawing Sheets

U.S. PATENT DOCUMENTS

| | | | |
|---|---|---|---|
| 5,690,629 A | | 11/1997 | Asher et al. |
| 5,695,504 A | * | 12/1997 | Gifford et al. ............... 606/153 |
| 5,695,524 A | * | 12/1997 | Kelley et al. ............... 606/219 |
| 5,816,471 A | | 10/1998 | Plyley et al. |
| 5,833,698 A | | 11/1998 | Hinchliffe |
| 5,899,904 A | | 5/1999 | Errico et al. |
| 5,976,159 A | | 11/1999 | Bolduc |
| 5,984,949 A | * | 11/1999 | Levin ......................... 606/216 |
| 5,993,464 A | | 11/1999 | Knodel |
| 6,036,700 A | | 3/2000 | Stefanchik |
| 6,165,204 A | | 12/2000 | Levinson et al. |
| 6,187,009 B1 | | 2/2001 | Herzog et al. |
| 6,187,019 B1 | | 2/2001 | Stefanchik |
| 6,193,734 B1 | | 2/2001 | Bolduc |
| 6,209,773 B1 | | 4/2001 | Bolduc |
| 6,514,263 B1 | | 2/2003 | Stefanchik |
| 6,520,973 B1 | | 2/2003 | McGarry |
| 6,530,932 B1 | | 3/2003 | Swayze |
| 6,726,695 B2 | * | 4/2004 | Tong ......................... 606/151 |

OTHER PUBLICATIONS

"510(k) Notification For the Cardica C-Port Anastomosis System", *Section 9, "Substantial Equivalence," and Appendices B, C, E,* (Unpublished).

* cited by examiner

ANASTOMOSIS STAPLE

FIELD OF THE INVENTION

The present invention relates generally to anastomosis, and more particularly to a staple used in an anastomosis procedure.

BACKGROUND

Anastomosis is a procedure where two separate tubular or hollow organs are surgically grafted together to form a continuous fluid channel between them. Vascular anastomosis between blood vessels creates or restores blood flow. When a patient suffers from coronary artery disease (CAD), an occlusion or stenosis in a coronary artery restricts blood flow to the heart muscle. In order to treat CAD, anastomosis is performed between a graft vessel and the affected coronary artery in order to bypass the occlusion and restore adequate blood flow to the heart muscle. This surgical procedure is known as a coronary artery bypass graft (CABG). Anastomosis may be performed in other surgical contexts, such as carotid artery bypass surgery or microvascular surgery.

Conventional anastomosis is performed by suturing two vessels together, which can be time-consuming and painstaking. More recently, anastomosis devices such as St. Jude Medical's SYMMETRY device have been introduced. These devices are noncompliant, meaning that the diameter of the device and hence the diameter of the anastomosis substantially does not change in use. However, a compliant anastomosis is preferred in many surgical situations, such as the distal anastomosis between a graft vessel and a coronary artery. A compliant anastomosis is capable of changing diameter in use, such as in response to blood flow pulsing through it. In a CABG procedure, many surgeons prefer the distal anastomosis to be compliant rather than noncompliant.

SUMMARY

In one aspect of the invention, an anastomosis staple has a base from which multiple tines extend. The base may be substantially rectangular, where one set of tines extends outward from locations in proximity to one edge of the base, and a second set of tines extends outward from locations in proximity to an opposite edge of the base. The end of at least one tine may be sharpened or pointed.

In another aspect of the invention, the first set of tines may be offset from the second set of tines. In this way, the tines do not interfere with one another as the staple is deployed.

In another aspect of the invention, the tines are moveable from a first configuration to a second configuration. For example, the first configuration may be an open configuration, in which the tines penetrate the walls of the graft vessel and the target vessel, and the second configuration may be a closed configuration, in which the tines are bent to secure the graft vessel to the target vessel. The tines may be moved from the first configuration to the second configuration at least partially as a result of contact with an anvil or other member.

In another aspect of the invention, the staple may include an alignment guide. The alignment guide may be an opening in the base, at least one element attached to the base, at least one element attached to the root of at least one tine, a combination thereof, or a different structure or mechanism. The alignment guide provides additional control over motion of the staple during deployment.

BRIEF DESCRIPTION OF THE DRAWINGS

The use of the same reference symbols in different figures indicates similar or identical items.

DETAILED DESCRIPTION

Referring to FIGS. 1-4, an exemplary anastomosis staple 2 is shown. The staple 2 includes a substantially rectangular base 4, where most or all of the base 4 is substantially planar and substantially the same thickness. Alternately, the base 4 is shaped differently. For example, the base 4 may be substantially square or trapezoidal, or may have different thicknesses at different locations along its surface. As another example, the base 4 may be substantially linear rather than substantially planar. Alternately, the base 4 of the staple 2 is curved such that it has substantially no planar surfaces. For example, the base 4 of the staple 2 may take the form of a right cylindrical tube cut in half lengthwise.

Figure 4:
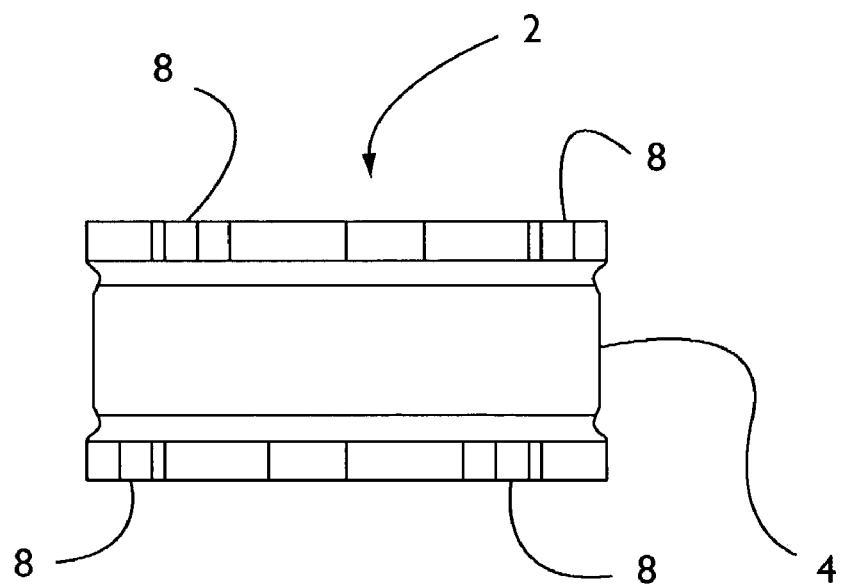
FIG. 4 is an end view of the anastomosis staple of FIG. 1.
Figure 4A:
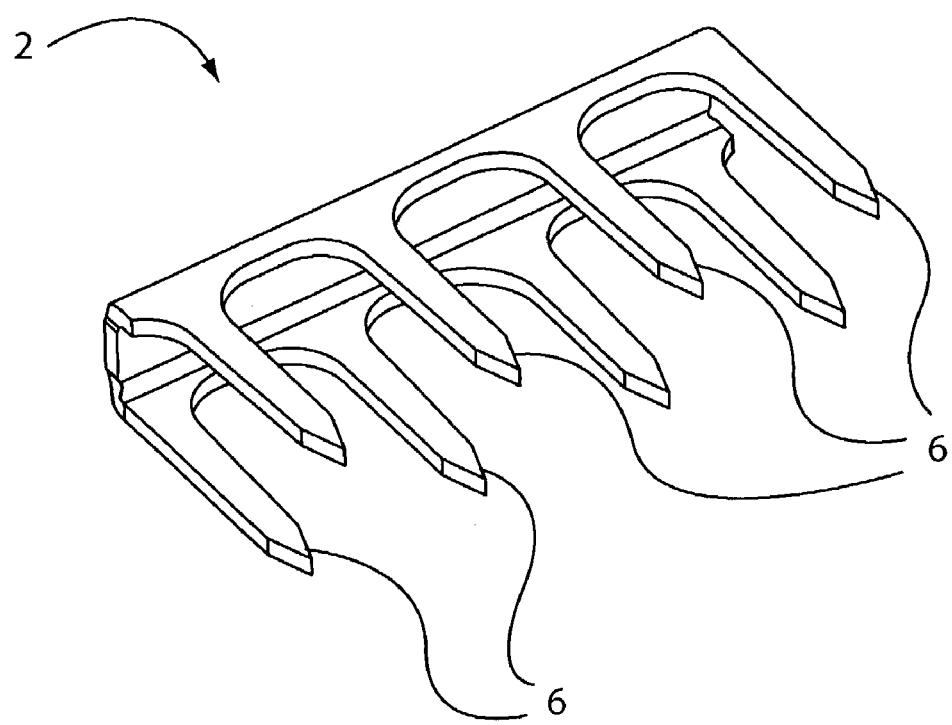
FIG. 4A is a perspective view of another configuration of the anastomosis staple.

Multiple tines 6 extend from the base 4. The base 4 has two opposite surfaces 5, and the tines 6 extend from one of those surfaces. Alternately, at least one tine 6 extends from each surface 5 of the base 4. Alternately, at least one tine 6 extends from a lateral surface 7 between the opposite surfaces 5. The longitudinal centerlines of the tines 6 are substantially parallel to one another. Alternately, the longitudinal centerline of at least one of the tines 6 is not substantially parallel to that of at least one of the other tines 6. Advantageously, four tines 6 are utilized in the staple 2. However, any other number of two or more tines 6 may be utilized instead. As an example, FIG. 4A shows a staple 2 having eight separate tines 6. The use of more than four tines 6 may provide greater holding power. Additionally, in certain applications, the use of more than four tines 6 may allow the staple 2 to hold two tissue structures together even if less than all of the tines penetrate both tissue structures. Where additional tines 6 are used, the base 4 of the staple 2 may be longer than it would be if fewer tines 6 were used.

The staple 2 is formed from 316 L stainless steel. Thus, the tines 6 are plastically deformable. Alternately, the staple 2 may be formed from a different type of stainless steel. Alternately, the staple 2 may be formed from a different biocompatible material or combination of biocompatible materials. For example, the staple 2 may be formed from a nickel-titanium alloy, or from a non-metallic material. The staple 2 may be plastically deformable or elastically deformable, depending on the material utilized. In an exemplary embodiment, the staple 2 is substantially 0.05 inches long, 0.04 inches wide, and 0.02 inches in height. These dimensions are small enough to allow the staple 2 to be used for anastomosis of a graft vessel to a coronary or a carotid artery, for end-to-end microvascular anastomosis, and in other applications involving small or delicate tissue structures. Alternately, the staple 2 may be sized differently.

Figure 5:
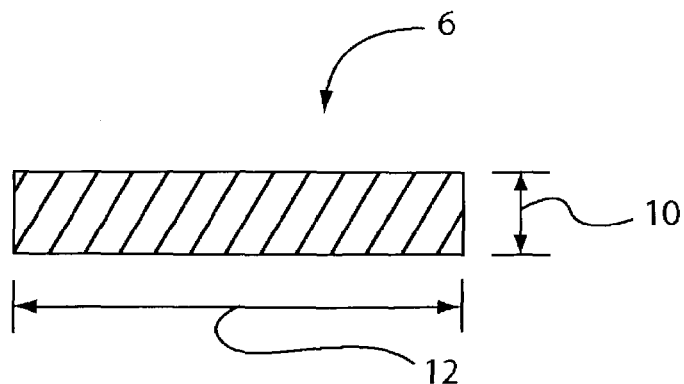
FIG. 5 is a cross-section view of one of the tines of the anastomosis staple of FIG. 1.

One or more of the tines 6 may be substantially the same thickness as the base 4, particularly where the base 4 and tines 6 are formed from a single sheet or piece of material. Referring to FIG. 5, a cross-section of one of the tines 6 is shown. All of the tines 6 have substantially the same cross-section. Alternately, at least one of the tines 6 has a different cross-section than at least one of the others. The cross-section is rectangular, such that the tine 6 has a height 10 and a width 12. The description of these dimensions as "height" and "width" does not limit the orientation of the staple 2 in use, and is utilized solely for clarity in describing the structure of the staple 2.

Each tine 6 extends a greater length from the base 4 than its height 10 or its width 12. Alternately, at least one tine 6 does not extend from the base 4 longer than its height 10 or width 12. Each tine 6 has a free end 8 opposite the end that is connected to the base 4. One or more of the tines 6 may be pointed, sharpened or otherwise shaped at its free end 8 to facilitate entry of the free end 8 into the tissue of the graft vessel and of the target vessel to be anastomosed together. One or more of the tines 6 may be tapered toward its free end 8, such that the height 10 and/or width 12 of the tine 6 decreases between the base 4 and the free end 8 of the tine 6. Further, one or more of the tines 6 may be tapered to a greater degree in proximity to its free end 8 in order to provide a sharp tooth or point at the free end 8. Further, if tapered, each tine 6 need not be tapered symmetrically or in a linear or constant manner. In addition, one or more of the tines 6 may be tapered differently than at least one of the other tines. Alternately, one or more of the tines 6 may be shaped differently. For example, at least one of the tines 6 may be radially symmetrical, with a circular, elliptical or other cross section.

Figure 2:
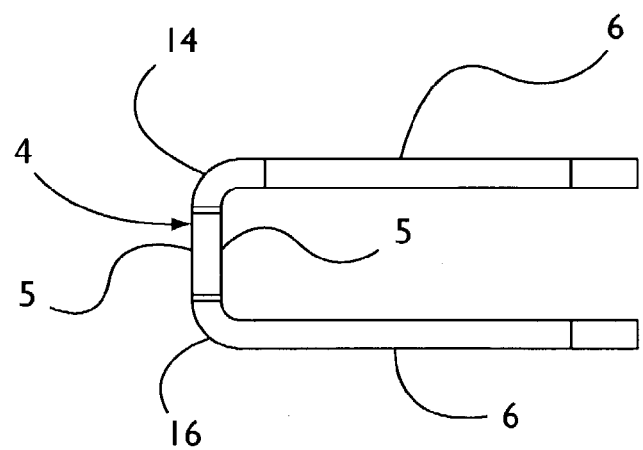
FIG. 2 is a side view of the anastomosis staple of FIG. 1.
Figure 3:
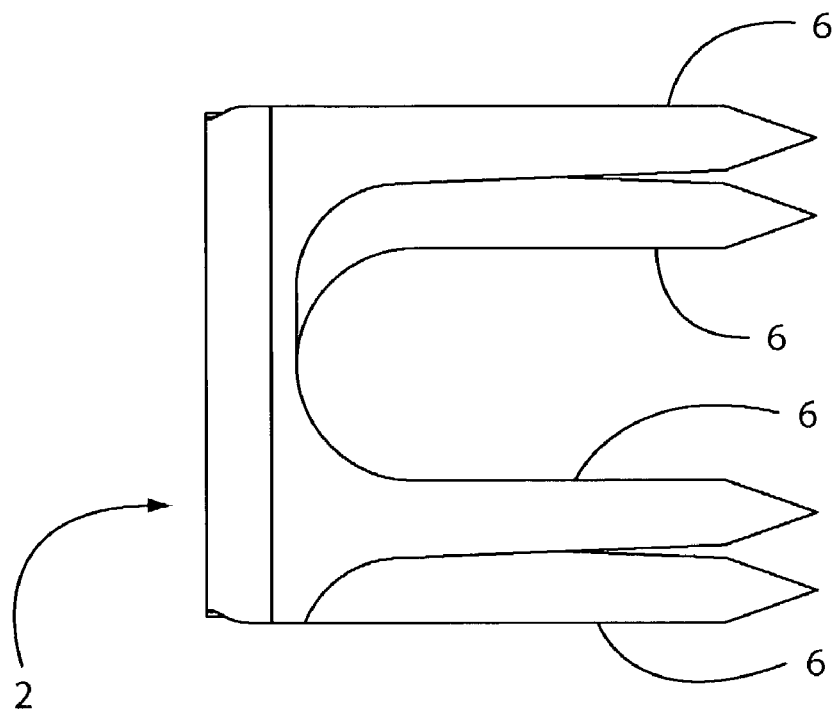
FIG. 3 is a top view of the anastomosis staple of FIG. 1.

Referring particularly to FIG. 2, the base 4 of the staple 2 has an upper edge 14 and a lower edge 16. The designations "upper" and "lower" are used here solely for clarity in describing the staple 2, and do not limit the orientations in which the staple 2 may be used. At least one tine 6 extends from a location at or near the upper edge 14 of the base 4. The upper edge 14 of the base 4 may be curved to provide a smooth transition between the base 4 and at least one tine 6. However, the upper edge 14 of the base 4 may be shaped differently, at least in part. At least one tine 6 extends from a location at or near the lower edge 16 of the base 4. The lower edge 16 of the base 4 may be curved to provide a smooth transition between the base 4 and at least one tine 6. However, the lower edge 16 of the base 4 may be shaped differently, at least in part.

Figure 1:
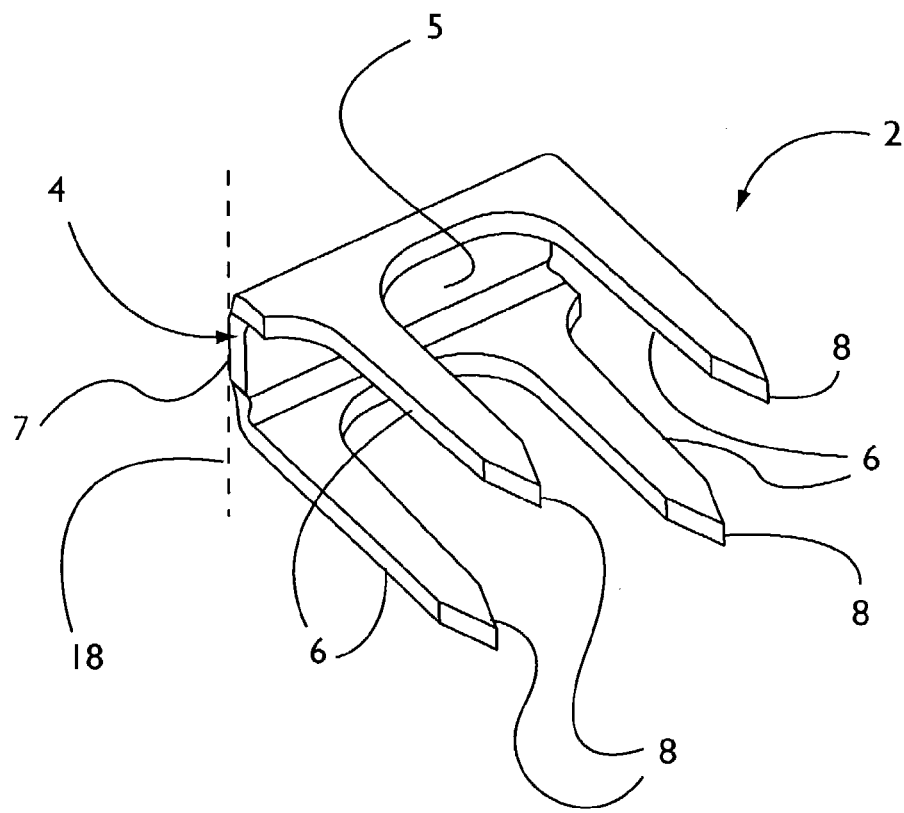
FIG. 1 is a perspective view of an anastomosis staple in a first configuration.

Referring also to FIG. 1, a line 18 extends along the lateral surface 7 of the base 4, and substantially perpendicular to both the upper edge 14 and to the lower edge 16 of the base 4. The line 18 may be positioned differently, if desired; its location relative to the base 4 is arbitrary. Each tine 6 along the upper edge 14 of the base 4 is positioned along that upper edge 14 at a distance from the line 18. Similarly, each tine 6 along the lower edge 16 of the base 4 is positioned along that lower edge 16 at a distance from the line 18. None of the tines 6 along the lower edge 16 of the base 4 are positioned at substantially the same distance from the line 18 as the tines 6 along the upper edge 14 of the base 4. That is, the tines 6 along the upper edge 14 of the base 4 are offset from the tines 6 along the lower edge of the base 4, to facilitate deployment of the staple 2, as described in greater detail below.

The width 12 of the tine 6 is greater than the height 10 of the tine 6. As a result, the moment of inertia of the tine 6 along an axis extending in the direction of the width 12 through the longitudinal centerline of the tine 6 is less than the moment of inertia of the tine 6 along an axis extending in the direction of the height 10 through the longitudinal centerline of the tine 6. As a result, when a force is applied to the tine 6, the tine 6 tends to bend in a direction in which the tine 6 has the lesser moment of inertia. Thus, the tine 6 is preferentially deformable in one of two directions substantially about an axis that passes through its longitudinal centerline and extends in the direction of the width 12 of the tine 6.

Figure 4B:
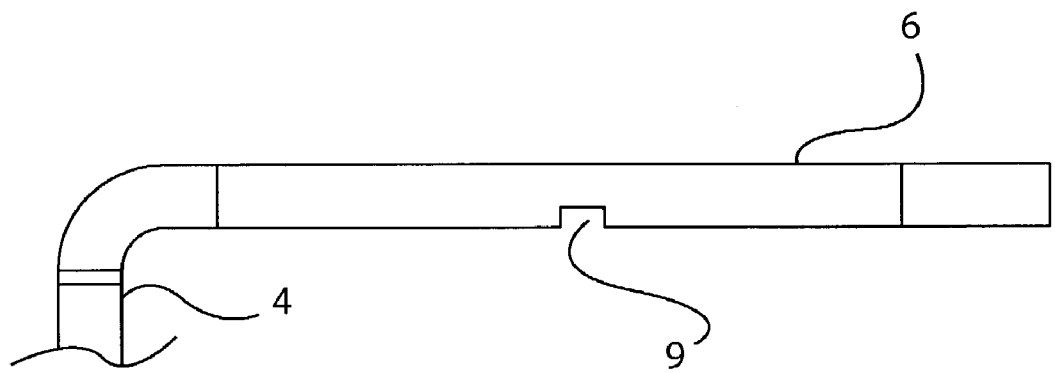
FIG. 4B is a detail view of the tine of the anastomosis staple of FIG. 1 or 4A, showing an optional notch therein.

A preferred bending direction for one or more tines 6 may be established to predict and/or control the deformation of the tines 6. The preferred bending direction may be established in several ways. As an example, the tines 6 may be used in conjunction with a corresponding anvil (not shown), where contact between the tines 6 and the anvil causes the tines 6 to bend in a preferred direction. The anvil may include pockets, depressions or other structures defined therein and/or thereon to receive the free end 8 of one or more tines 6 and guide the bending of the tines 6 in a preferred direction. As another example of establishing a preferred bending direction, referring also to FIG. 4B, one or more of the tines 6 may include one or more notches 9 or other sources of stress or bending concentration defined therein. Each notch 9 extends along a direction parallel to the dimension of width 12 of the tine 6. The notches 9 act to concentrate bending at the location of the notch 9. Thus, the presence of at least one notch 9 in a tine 6 defines a preferred bending direction for that tine 6. Consequently, each notch 9 is provided on a tine 6 in a location that results in desired bending characteristics for that tine 6. As another example, one or more of the tines 6 may be pre-bent. A pre-bent tine 6 is not entirely straight in a first configuration prior to deployment instead, it is curved, kinked, or angled partially in the direction in which the tine 6 is desired to bend. Individual portions of the pre-bent tine 6 may be straight. For example, a pre-bent tine 6 may include two straight portions connected to one another at an angle. In this way, force applied to the tine 6 bends the tine 6 further in the direction in which it is pre-bent. Thus, the pre-bent tine 6 has a preferred bending direction. Two or more structures, mechanisms or methods may be combined to provide a preferred bending direction for one or more tines 6. For example, one or more tines 6 may include a notch 9 defined therein, where the tines 6 are additionally brought into contact with an anvil for deployment.

As shown in FIGS. 1-4, the tines 6 are in a first configuration for penetration into a graft vessel and a target vessel. The staple 2 may be deployed into tissue such that the free ends 8 of the tines 6 enter and/or penetrate through the tissue of both the graft vessel and the target vessel. In an exemplary embodiment, an end of the graft vessel is placed against a side of the target vessel. The end of the graft vessel may be incised to form two or more flaps configured for placement against the outer surface of the target vessel, such that the staples 2 penetrate the flaps and the tissue of the target vessel adjacent to the flaps. An opening in the wall of the target vessel may be made before or after placing the end of the graft vessel against the side of the target vessel, to allow fluid to flow between the vessels.

Figure 6:
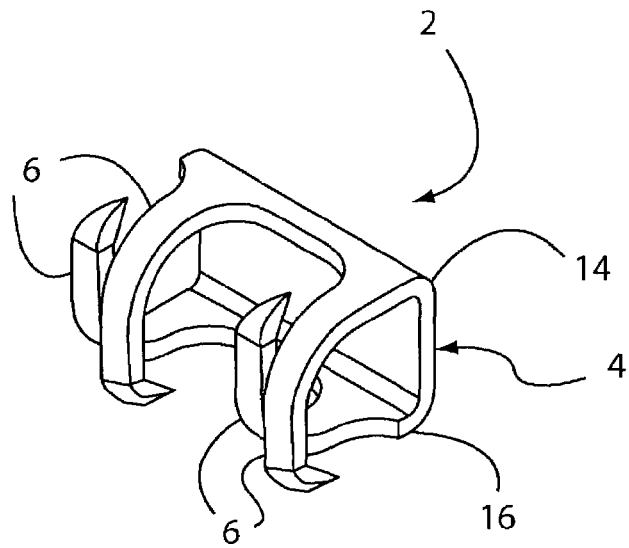
FIG. 6 is a perspective view of the anastomosis staple of FIG. 1 in a second configuration.
Figure 7:
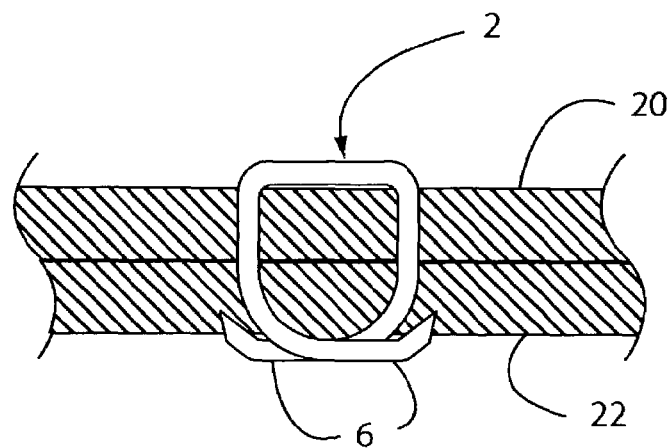
FIG. 7 is a cross-section of the anastomosis staple of FIG. 1 deployed in tissue in the second configuration.

After the tines 6 have penetrated the tissue of the graft vessel and of the target vessel, the tines 6 are moveable to a second configuration, shown in FIGS. 6-7. In the second configuration, the staple 2 secures tissue of the graft vessel 20 to tissue of the target vessel 22. The tines 6 extend through the walls of both vessels 20, 22, substantially preventing slippage of the vessels 20, 22 relative to one another. The distal portions of the tines 6 extend into the lumen of the target vessel 22. The distal tip of at least one tine 6 may curve, bend or otherwise extend into the wall of the target vessel 22 in the second configuration, in order to secure the staple to the target vessel 22 more completely. Thus, the distal tip of at least one tine 6 may be positioned within the wall of the target vessel 22 in the second configuration. The distal tips of the tines 6 need not curve into the target vessel 22 in the second configuration in order to secure the graft vessel to the target vessel. For example, the distal portion of at least one tine 6 may be bent to a position substantially parallel to the inner surface of the target vessel 22 in the second configuration.

At least the distal portion of each tine 6 plastically deforms away from its position in the first configuration to the position that it occupies in the second configuration. The distal portion of each tine 6 advantageously deforms at least partially in a preferred bending direction. The staple 2 may be used with an anvil (not shown) such as, but not limited to, one of the anvils described in U.S. Pat. Nos. 6,391,038 and 6,398,797, and in U.S. patent application Ser. No. 10/151,441, which are herein incorporated by reference in their entirety. As the staple 2 is urged toward the anvil, contact between the staple 2 and the anvil results in a transition from the first configuration of the staple 2 to the second configuration of the staple 2. The shape of the anvil and/or indentations or structures in or on the anvil may play a role in determining the direction in which each tine 6 of the staple 2 bends. That is, the direction of deformation of one or more tines 6 may be determined at least in part by the interaction between one or more tines 6 and the anvil. Deformation of the tines 6 may be caused by contact between the tines 6 and an anvil, by the presence of notches 9 or other sources of stress or bending concentration in the tines 6, by pre-bending at least one tine 6, by a combination of these factors, or by other or additional structures, mechanisms or methods. Multiple staples 2 may be deployed through contact with the anvil.

Tines 6 that extend from the upper edge 14 of the base 4 are deformed toward tines 6 that extend from the lower edge 16 of the base 4, and tines 6 that extend from the lower edge 16 of the base 4 are deformed toward tines 6 that extend from the upper edge 14 of the base 4. That is, tines 6 that extend from different edges 14, 16 of the base 4 are deformed toward each other. This is at least partially a consequence of the preferred bending direction of the tines 6. Because the tines 6 are offset from one another, opposing tines 6 may contact one another, without substantially interfering with one another, during deployment from the first configuration to the second configuration. Thus, the tines 6 are spaced apart from one another in the second configuration. In the second configuration, the tines 6 each lie in a plane that is substantially coplanar with planes in which the other tines 6. Alternately, in the second configuration at least one tine 6 lies in a plane that is not substantially coplanar with a plane in which at least one other tine 6 lies.

Alternately, opposing tines 6 are offset such that they do not substantially contact one another during deployment from the first configuration to the second configuration. Alternately, tines 6 that extend from the upper edge 14 of the base 4 are deformed away from tines 6 that extend from the lower edge 16 of the base 4, and tines 6 that extend from the lower edge 16 of the base 4 are deformed away from tines 6 that extend from the upper edge 14 of the base 4. That is, tines 6 that extend from different edges 14, 16 of the base 4 are deformed away from each other. This is at least partially a consequence of the preferred bending direction selected for the tines 6.

The anvil may include half as many pockets as the number of tines 6 on the staple 2. These pockets are configured such that each pair of corresponding tines 6 extending from opposite edges 14, 16 of the base 4 thus encounters the same pocket. During deformation, the tines 6 pass each other in the middle of the pocket under the now-captured tissue. Alternately, the pockets on the anvil may be configured differently, or not used. For example, where an odd number of tines 6 are provided, the anvil includes a number of pockets unequal to half the number of tines 6. The tines 6 may be configured to pass close to one another during deployment from the first configuration to the second configuration. That is, a tine 6 extending from the upper edge 14 of the base 4 is deployed generally toward a corresponding offset tine 6 extending from the lower edge 16 of the base 4. As these corresponding tines 6 bend toward one another, the distal end of each tine 6 moves at least partly in a direction opposite to the direction of motion of the other tine 6. As the tines 6 penetrate the walls of the vessels 20, 22, friction is present between the tines 6 and those walls. Thus, the distal end of each tine 6 tends to push tissue of the vessels 20, 22 toward the distal end of the corresponding tine 6. That is, each tine 6 forces the tissue being punctured toward the opposite tine 6. As a result, by configuring corresponding tines 6 to pass close to one another during deployment, the vessels 20, 22 can be secured together more effectively. Alternately, two or more of the tines 6 are configured to contact or interfere at least partially with one another during deployment. In such an embodiment, at least one tine 6 may be configured to connect securely and/or positively to at least one other tine 6 upon deployment.

As another example, the staple 2 may be formed from nickel-titanium alloy or other material capable of being elastically deformed between two stable states. In such an exemplary embodiment, the first configuration and the second configuration are the two stable states of the staple 2, and the staple 2 elastically deforms from the first configuration to the second configuration. Upon application of a force to, or removal of a force or restraint from the staple 2, the staple 2 elastically deforms to the stable second configuration. Other configurations of the staple 2 may be utilized, if desired.

In the second configuration, the distal portion of at least one tine 6 may be positioned against, or dig into, the inner surface of the wall of the target vessel 22. Where the staples 2 are used to connect two blood vessels, this close contact between the distal portion of each tine 6 and the inner surface of the wall of the target vessel 22 reduces the amount of material of the tine 6 that is exposed to the bloodstream, thereby reducing the possibility of clotting. Further, in the second configuration, the free end 8 of at least one of the tines 6 may penetrate the wall of the target vessel 22. In this way, the tines 6 may hold the tissue of the target vessel 22 more securely, and the amount of material of the tine 6 that is exposed to the bloodstream is further reduced. Alternately, the free ends 8 of the tines 6 do not penetrate the target vessel 22, and the distal portions of the tines 6 are substantially parallel to the inner surface of the target vessel 22.

In the second configuration, the base 4 of the staple 2 is positioned substantially parallel to and in contact with the outer surface of the graft vessel 20. Alternately, the base 4 may be positioned differently relative to the outer surface of the graft vessel 20, and/or may be spaced apart at least in part from the outer surface of the graft vessel 20. The staple 2 is deployed such that the tines 6 penetrate both the graft vessel 20 and the target vessel 22 from the outside. However, the staple 2 may be deployed such that the tines 6 penetrate the graft vessel 20 and the target vessel 22 from the inside, such that the base 4 of the staple 2 is located inside the lumen of the target vessel 22. Advantageously, a number of staples 2 are deployed around the perimeter of the anastomosis, in order to thoroughly secure the vessels 20, 22 together and to minimize or eliminate any leakage at the anastomosis site.

Optionally, one or more alignment guides (not shown) may be provided. As one example, one or more flanges or other structures (not shown) may extend from the base 4 of the staple 2. One or more grooves may be provided in a deployment device (not shown), where each flange slides along a corresponding groove in order to stabilize, align, orient or otherwise control the motion of the staple 2 during deployment. The particular shape of each flange and/or corresponding groove is not critical to the invention. Alternately, a gripping device or other mechanism in or on a deployment tool may hold one or more flanges of each staple 2, such that the deployment tool can stabilize, align or otherwise guide the staple 2 in the desired direction during deployment. At least one of the flanges may be shaped differently than at least one of the others, which may advantageously be used to register the staples 2 in a particular orientation relative to the deployment tool. As another example, one or more flanges or other structures may extend from the root of at least one tine 6. The root of the tine 6 is the portion of the tine 6 in proximity to the base 4. By placing one or more flanges on the root of at least one tine 6, those flanges substantially do not affect the ability of the distal end of the tine 6 to bend in the manner described above. The flange or flanges may be used in conjunction with one or more gripping devices, grooves, other structures or mechanisms, or a combination thereof provided in conjunction with a deployment device. As another example, the alignment guide or guides may be one or more passages defined through the base 4 of the staple 2. A rail, spike or other structure or mechanism on a deployment tool may extend through each passage, where the staple 2 is moveable relative to it. Thus, the deployment tool can stabilize, align or otherwise guide the staple 2 in the desired direction during deployment. Each passage may be rectangular, circular, elliptical, polygonal, or shaped in a different way. Further, at least one of the passages through the base 4 of the staple 2 may be shaped differently than at least one of the others. That difference in shape may be used to register each staple 2 in a particular orientation relative to the deployment tool. The particular shape of the passage or passages is not critical to the invention. As another example, the alignment guide or guides may be at least one notch, depression or similar structure in the base 4 of the staple 2, where the notch engages a rail, spike or other structure or mechanism on the deployment tool.

Figure 8:
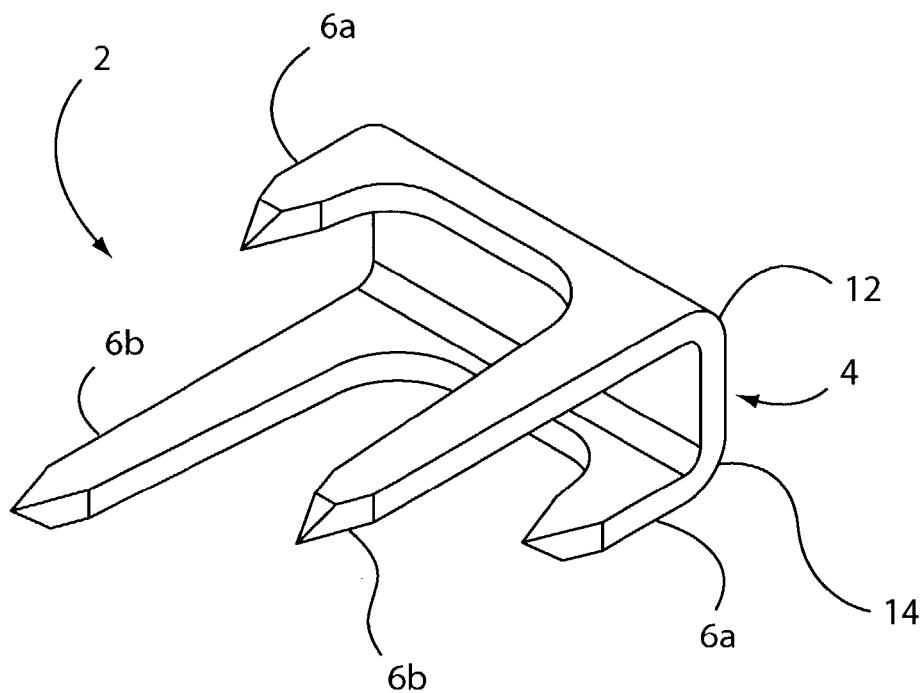
FIG. 8 is a perspective view of an alternate configuration of an anastomosis staple.

Referring to FIG. 8, an alternate anastomosis staple 2 is shown. The staple 2 includes short tines 6a and long tines 6b extending from the base 4. Each short tine 6a extends from an edge 12, 14 of the base 4, and a long tine 6b extends from the opposite edge 12, 14 of the base 4. Each short tine 6a is not offset from the corresponding long tine 6b. The short tine 6b is short enough such that its deformation to a second configuration from a first configuration does not interfere with the corresponding long tine 6a, even though the corresponding tines 6a, 6b are not offset from one another. Thus, the short tine 6b presses tissue against the corresponding long tine 6a without contacting or interfering with that long tine 6a. Alternately, the short tines 6a are configured to interfere with the long tines 6b in the second configuration. Alternately, at least one pair of corresponding tines 6a, 6b may be offset from one another, if desired. While four tines 6 are shown in FIG. 8, more or fewer tines 6 may be used.

Figure 9:
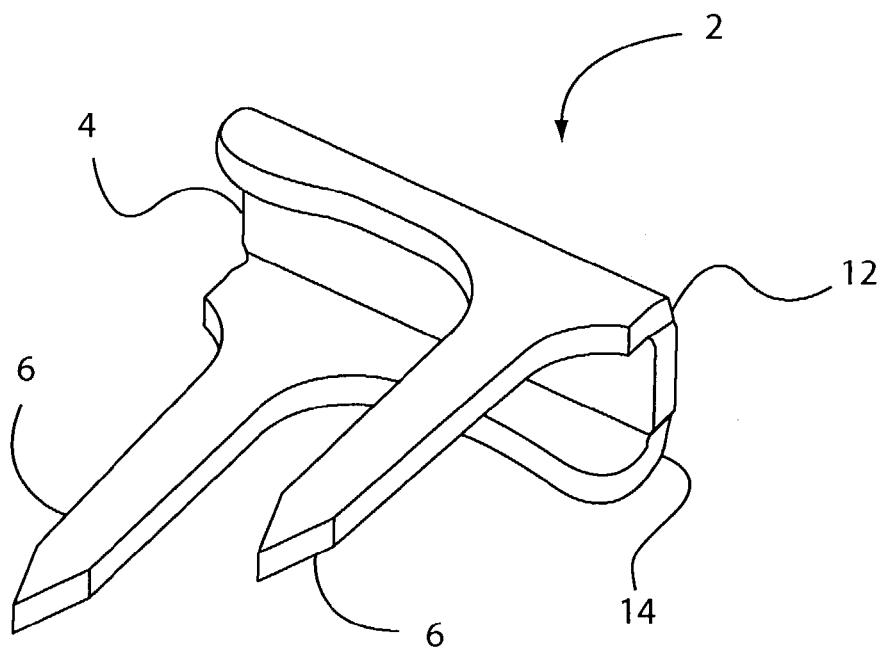
FIG. 9 is a perspective view of another configuration of an anastomosis staple.

Referring to FIG. 9, an alternate anastomosis staple 2 is shown. Two tines 6 are used, where each tine 6 extends from a different edge 12, 14 of the base 4. The base 4 is substantially planar, and the tines 6 extend substantially from different corners of the base 4. For example, where the base 4 is rectangular, the tines 6 extend substantially from opposite corners of the base 4. The base 4 may be shaped differently, if desired. The tines 6 are spaced apart from one another, such that the tines 6 are not in relative proximity to one another and do not interfere with one another in the second configuration.

Figure 10:
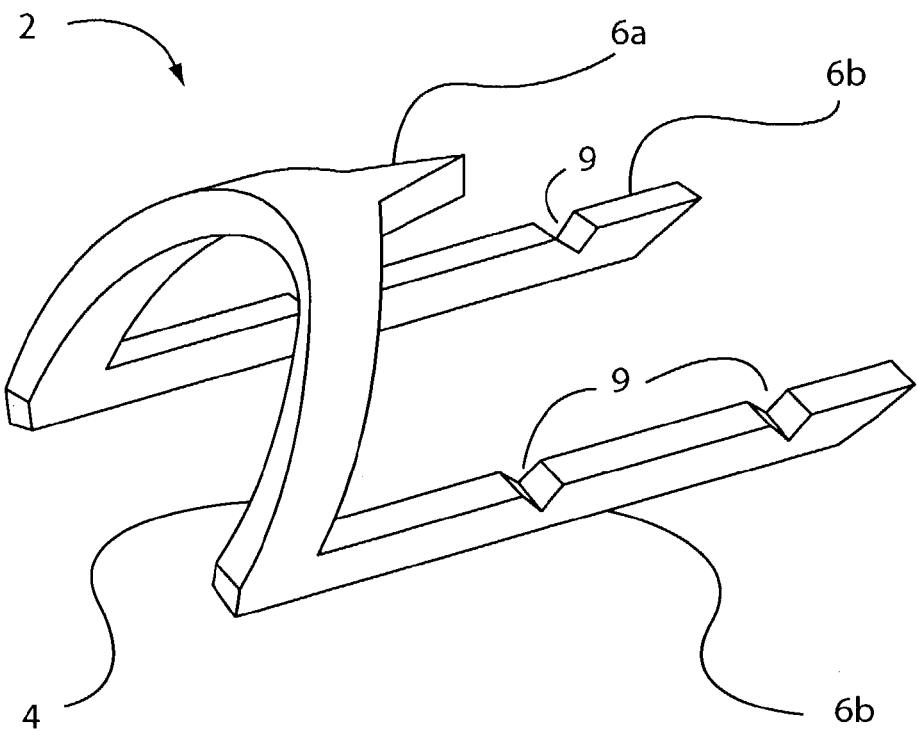
FIG. 10 is a perspective view of another configuration of an anastomosis staple.
Figure 11:
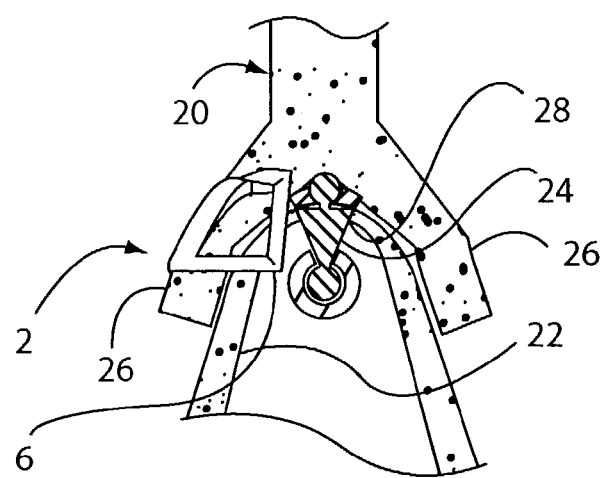
FIG. 11 is a side cutaway view of the staple of FIG. 10 deployed into tissue.

Referring to FIGS. 10-11, another alternate anastomosis staple 2 is shown. The staple 2 may be cut from a stainless steel tube, such as by laser cutting. Thus, the base 4 of the staple 2 has a curved shape that may substantially take the form of a parabola, hyperbola, semicircle, a combination of these shapes, or a different curved shape. The base 4 has two ends, and a tine 6b extends from each end of the base 4. Alternately, additional tines 6b may extend from the base 4. In the first configuration, the tines 6b are substantially parallel to one another, and extend in substantially the same direction. One or more notches 9 are defined in at least one tine 6b, such that bending of each tine 6b is concentrated at the notch or notches 9. An additional tine 6a extends from the apex of the base 4. The tine 6a is shorter than the tines 6b, and may be a spike or other structure different from that of the tines 6b. The short tine 6a may extend from the base 4 at a location other than its apex, and more than one short tine 6a may be used. Alternately, the tine or tines 6 at the apex of the base 4 is a tine 6b, having a configuration the same as or similar to the other tines 6b. The longer tine 6b allows for additional penetration of tissue at the apex of the base 4.

To begin the anastomosis procedure, flaps 26 are formed at an end of the graft vessel 20, which is placed against a side of the target vessel 22. Placement of the flaps 26 against a side of the target vessel 22 is performed as part of the anastomosis procedure, regardless of the configuration of staple 2 utilized. However, other configurations of the graft vessel 20 and the target vessel 22 may be used, if desired.

Each staple 2 is deployed by urging the tines 6b toward an anvil 24 positioned within the lumen of the target vessel 22. The tines 6b penetrate the flaps 26 of the graft vessel 20 and the wall of the target vessel 22, then encounter the anvil 24. As the tines 6b continue to be urged forward, contact between the tines 6 and the anvil 24 causes the tines 6b to bend at the notches 9. This bending continues as the staple 2 continues to move forward. When deployment is complete, the distal ends of the tines 6b have been bent back into the wall of the target vessel 22, and each may penetrate into a flap 26 of the graft vessel 20 as well. Further, the short tine 6a may penetrate or press against a flap 26 of the graft vessel 20 to press tissue of the vessels 20, 22 against the distal ends of the tines 6b. Where a third tine 6b is used instead of the short tine 6*a*, that third tine 6*b* also may include one or more notches 9. A number of staples 2 may be utilized to connect the vessels 20, 22. An aperture 28 or other opening is created in the wall of the target vessel 22 at its connection with the end of the graft vessel 20 before, during or after the deployment of the staple or staples 2.

As shown most clearly in FIG. 11, the staple 2 is oriented relative to the vessels 20, 22 such that each pair of corresponding tines 6 extending from opposite edges 14, 16 can be characterized as vertically oriented. That is, within a pair of corresponding tines 6, one tine 6 is closer to the end of the graft vessel 20 than the other tine. The term "vertically oriented" is used for convenience in describing the orientation of the pairs of corresponding tines, and does not limit the placement or orientation of the staple 2 within a patient. The vertical orientation of the tines 6 facilitates holding the flaps 26 of the graft vessel 20 firmly against the wall of the target vessel, thereby minimizing or eliminating leakage. Additionally, the vertical orientation of the tines 6 allows the tines 6 to engage and hold the area of the target vessel 22 that is in proximity to the aperture 28 therein. This engagement reduces the motion of the area of the target vessel 22 that is in proximity to the aperture 28, where that motion is a result of fluid flow through the anastomosis site. Thus, the vertical orientation of the tines 6 reduces turbulence at the anastomosis site. Alternately, the pairs of corresponding tines 6 may be oriented differently relative to the centerline of the target vessel.

The staple 2 described above may be used to perform distal anastomosis (that is, anastomosis between a graft vessel and a coronary artery) or proximal anastomosis (that is, anastomosis between a graft vessel and the aorta). Further, the staple 2 described above may be used for surgical procedures other than CABG procedures, such as carotid artery bypass surgery, peripheral vascular surgery, neurovascular surgery, or transplant surgery.

While the invention has been described in detail, it will be apparent to one skilled in the art that various changes and modifications can be made and equivalents employed, without departing from the present invention. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A method of performing anastomosis between a graft vessel and a target vessel, comprising:
   providing at least one anastomosis staple in a first configuration, said anastomosis staple comprising a substantially rectangular base having a first edge and a second edge substantially parallel to one another, and a third edge substantially perpendicular to said first and said second edges; and at least three deformable tines, said tines extending from said first and second edges of said base; wherein no said tine that extends from said first edge is positioned at substantially the same distance from said third edge as any said tine that extends from said second edge;
   placing an end of the graft vessel against a side of the target vessel;
   deploying said anastomosis staple into the tissue of the graft vessel and the target vessel; and
   deforming said tines to a second configuration.

2. The method of claim 1, wherein at least part of at least one said tine is located within a lumen of the target vessel in said second configuration.

3. The method of claim 1, wherein the distal end of at least one said tine is located within the wall of the target vessel in said second configuration.

4. The method of claim 1, wherein said deforming comprises applying a force to said anastomosis staple.

5. The method of claim 1, further comprising incising the end of the graft vessel to create at least two flaps, wherein said placing comprises placing said flaps against an outer surface of the target vessel.

6. The method of claim 1, wherein said deforming comprises deforming at least one said tine in a preferred bending direction.

* * * * *